United States Patent
Doerr

(10) Patent No.: US 9,393,436 B2
(45) Date of Patent: Jul. 19, 2016

(54) IMPLANTABLE CARDIOVERTER-DEFIBRILLATOR INCLUDING ARRHYTHMIA DETECTION CRITERIA

(71) Applicant: BIOTRONIK SE & CO. KG, Berlin (DE)

(72) Inventor: Thomas Doerr, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 0 days.

(21) Appl. No.: 14/504,406

(22) Filed: Oct. 1, 2014

(65) Prior Publication Data

US 2015/0100101 A1 Apr. 9, 2015

Related U.S. Application Data

(60) Provisional application No. 61/888,002, filed on Oct. 8, 2013.

(30) Foreign Application Priority Data

Oct. 8, 2013 (EP) .................................. 13187664

(51) Int. Cl.
*A61N 1/39* (2006.01)
(52) U.S. Cl.
CPC ............ *A61N 1/3962* (2013.01); *A61N 1/3981* (2013.01); *A61N 1/3987* (2013.01)
(58) Field of Classification Search
CPC .. A61N 1/3962; A61N 1/3981; A61N 1/3987
USPC .......................................................... 607/4–5
See application file for complete search history.

(56) References Cited

U.S. PATENT DOCUMENTS

| 6,718,204 | B2 | 4/2004 | DeGroot et al. |
| 8,229,563 | B2 | 7/2012 | Warren et al. |
| 8,249,702 | B2 | 8/2012 | Warren et al. |
| 2006/0241701 | A1* | 10/2006 | Markowitz ............. A61N 1/025 607/5 |
| 2007/0088394 | A1* | 4/2007 | Jacobson ............. A61N 1/3704 607/4 |
| 2007/0219456 | A1 | 9/2007 | Thompson |
| 2007/0270911 | A1 | 11/2007 | Doerr |
| 2010/0331904 | A1 | 12/2010 | Warren et al. |
| 2012/0316612 | A1 | 12/2012 | Warren et al. |
| 2012/0323290 | A1 | 12/2012 | Warren et al. |
| 2013/0158615 | A1 | 6/2013 | Mahajan et al. |

FOREIGN PATENT DOCUMENTS

EP          0547733 A2     6/1993

OTHER PUBLICATIONS

European Search Report, dated Dec. 15, 2014, 8 pages.
European Search Report, dated Dec. 10, 2013, 8 pages.

* cited by examiner

*Primary Examiner* — Paula J Stice
(74) *Attorney, Agent, or Firm* — ARC IP Law, PC; Joseph J. Mayo

(57) ABSTRACT

An implantable cardioverter-defibrillator system that includes at least one or more stimulation units, one or more detection units, one or more control units, two or more electrode poles and one or more high voltage capacitors. The at least one control unit is connected with the at least one stimulation unit, and the at least one control unit is connected with at the least one detection unit. The two or more electrode poles are in contact with body tissue, and the one or more high voltage capacitors are charged by at least one charging unit, wherein the at least one charging unit is connected to the at least one control unit.

16 Claims, 5 Drawing Sheets

IMPLANTABLE CARDIOVERTER-DEFIBRILLATOR INCLUDING ARRHYTHMIA DETECTION CRITERIA

This application claims the benefit of U.S. Provisional Patent Application 61/888,002 filed on 8 Oct. 2013, and European Patent Application 13187664.1 filed on 8 Oct. 2013, the specifications of which are hereby incorporated herein by reference.

BACKGROUND OF THE INVENTION

1. Field of the Invention

Embodiments of the invention generally relate to a heart stimulator with a stimulation unit connected to a stimulation electrode to stimulate a ventricle of a heart.

2. Description of the Related Art

Typically, a stimulation unit is designed to generate both stimulation pulses and antitachycardic defibrillation shocks, and for this purpose has at least one high voltage capacitor in which the electricity required for an antitachycardic defibrillation shock may be stored. Generally, the heart stimulator also has a detector, which is designed to process physiological signals received from the heart, and on the basis of these signals detects the presence of an acute ventricular tachycardia or fibrillation. Typically, a further component of the heart stimulator is a control unit which is connected to the detector and the stimulation unit and which is designed to respond to an output signal of the detector, and to actuate the stimulation unit either to emit a train of stimulation pulses forming an antitachycardic therapy (antitachycardic pacing therapy, ATP) or an antitachycardic defibrillation shock.

Such heart stimulators are generally referred to as implantable cardioverter defibrillators (ICD's). The heart stimulators referred to herein are therefore typically primarily implantable heart therapy devices which are capable of treating a heart tachycardia.

Within the scope of this application tachycardias are generally understood to mean both tachycardias in the narrower sense, which are characterized by a stable cardiac rhythm with a pathologically high frequency, and fibrillations also called unstable tachycardia. Typical therapies, which may be provided by a heart stimulator of the type already mentioned, are antitachycardic stimulation or antitachycardic defibrillation shock.

An antitachycardic defibrillation shock is generally an electric current surge which is transmitted to the heart and which has a sufficiently high voltage and energy to fully excite a ventricle affected by fibrillation and therefore to render it refractory. Generally, circulating excitations typical of fibrillations are interrupted in this manner. In the case of a tachycardia in the narrower sense, which is often also referred to as ventricular tachycardia, if the ventricle is affected, and which is abbreviated to VT or stable VT (as opposed to ventricular fibrillation VF or unstable VT), successful therapy using antitachycardic stimulation (anti tachyarrhythmia pacing; ATP) is often possible, especially for stable VT. In antitachycardic stimulation, the heart stimulator typically emits a series of stimulation pulses whose energy is much lower than the energy of an antitachycardic defibrillation shock and which are generally not painful either. In antitachycardic stimulation, such stimulation pulses of comparatively lower energy are typically emitted with a frequency that exceeds the frequency of the recorded tachycardia. Generally, the anti tachyarrhythmia pacing is also called ATP or ATP one shot. Typically, in many cases a tachycardia may be terminated in this manner without the patient suffering pains or without the energy requirement being particularly high.

Since success with an antitachycardic stimulation is not always achieved, it may be necessary to give an antitachycardic defibrillation shock following unsuccessful antitachycardic stimulation (ATP).

For example, U.S. Pat. No. 6,718,204 entitled "Method and Apparatus to Control Delivery of High-Voltage and Anti-Tachy Pacing Therapy in an Implantable Medical Device", to Degroot et al., discloses a method for giving such antitachycardic stimulation after a tachycardia is detected, during or shortly before a high voltage capacitor is charged, such that antitachycardic defibrillation shock may be given after the tachycardic stimulation if necessary.

In Degroot et al., there appears to be contradictory requirements of wanting to save as much as possible on the one hand, i.e. avoiding charging the high voltage capacitor wherever possible, and on the other hand being able to give an antitachycardic defibrillation shock as soon as possible after an unsuccessful antitachycardic stimulation, which in principle presupposes a capacitor that is already charged.

For example, a possible solution to the above mentioned dilemma may be found in United States Patent Publication 2007/0270911 entitled "Heart Stimulator", to Doerr et al., which discloses discontinuing charging of a high voltage capacitor in case of a terminated tachycardia.

Generally, also relevant for the antitachycardia therapy are the criteria for discriminating a tachycardia from a fast but still tolerable heart rhythm or non-sustained arrhythmia to decrease the number of inadequate antitachycardia defibrillation shock therapies. For example, U.S. Pat. No. 8,229,563 entitled "Devices for Adapting Charge Initiation for an Implantable Cardioverter-Defibrillator", U.S. Pat. No. 8,249,702 entitled "Method for Adapting Charge Initiation for an Implantable Cardioverter-Defibrillator", United States Patent Publication 2012/0323290 entitled "Methods and Devices for Adapting Charge Initiation for an Implantable Defibrillator", and United States Patent Publication 2012/0316612 entitled "Methods and Devices for Adapting Charge Initiation for an Implantable Defibrillator", all to Warren et al., disclose an increasing X out of Y criteria, to enhance the reliability of arrhythmia detection.

BRIEF SUMMARY OF THE INVENTION

According to one or more embodiments of the invention, the inventor has recognized that elongated or prolonged detection or elongated or prolonged detection time or elongated or prolonged VF-detection counter, as it is induced by increasing the X and Y of an X out of Y criteria, may increase the reliability of the tachycardia detection, but may also decrease the probability of a successful antitachycardia pacing (ATP).

One or more embodiments of the invention include an implantable cardioverter-defibrillator system (ICDS), which utilizes a criteria to identify an arrhythmia, for example a VT, before delivering or emitting an ATP therapy, and a different criteria to identify an arrhythmia, for example a VT, before delivering an antitachycardia defibrillation shock therapy.

At least one embodiment of the invention includes an implantable cardioverter-defibrillator system (ICDS) with at least one or more of one or more stimulation units, one or more detection units, at least one control unit, wherein the at least one control unit may be connected with the at least one stimulation unit and the at least one control unit may be connected with at the least one detection unit, two or more electrode poles, wherein the two or more electrode poles may be in contact with body tissue, and one or more high voltage capacitors which may be charged by one or more charging units, and wherein the at least one charging unit may be connected to the at least one control unit or the at least one stimulation unit or both, and wherein one or both of the least one control unit or the at least one stimulation unit may initiate the charging of the at least one high voltage capacitor by the at least one charging unit, wherein the at least one detection unit may process physiological signals received from the heart and may detect the presence of an acute ventricular tachycardia or fibrillation, wherein these physiological signals are one or more of accelerations, sounds, and electric signals such as bioelectric potentials, currents and impedances, wherein at least one of the two or more electrode poles may sense electric signals, wherein the physiological signals or data representing such physiological signals may be transmitted to the control unit by the detection unit utilizing an output signal, wherein the at least one control unit may respond to the output signal of the at least detection unit and may actuate the at least one stimulation unit to emit stimulation pulses or a train of stimulation pulses forming an antitachycardic therapy (ATP), or to emit an antitachycardiac defibrillation shock, wherein the at least one control unit may actuate an ATP prior to actuating an antitachycardiac defibrillation shock, wherein the charging of the at least one high voltage capacitor may be initiated either prior to actuating an ATP or during emitting an ATP or after emitting an ATP, wherein the at least one control unit may actuate the at least one stimulation unit dependent on preset criteria or an adaptive criteria, wherein the preset or adaptive criteria may be different when actuating an ATP and when actuating an antitachycardiac defibrillation shock, and wherein the criteria when actuating an ATP is a M out of N criteria and the criteria when actuating an antitachycardiac defibrillation shock is a X out of Y criteria, wherein at least X>M and Y>N.

At least one embodiment of the invention allows increasing the reliability of the tachycardia detection before applying an antitachycardia defibrillation shock without delaying the emitting of the ATP therapy.

By way of one or more embodiments, the two or more electrode poles may be positioned on one or more electrode cables, which are connectable or connected with the ICDS, or the two or more electrode poles may be positioned on one or more implantable device, wherein at least one of the implantable devices may include an ICDS or ICD.

In at least one embodiment, the one or more detection units, the one or more stimulation units and the one or more control unit may be, as described, three modules, or the detection unit, the one or more stimulation units and the control unit may be incorporated in a single module or in any number of modules necessary to implement the described functions.

In one or more embodiments, a quotient of X/Y may exceed the quotient of M/N, or the M out of N criteria may be changed if a preset number of unsuccessful ATP has been actuated by decreasing the quotient M/N or by decreasing N while the quotient M/N is kept constant.

In at least one embodiment of the invention, the quotient of X/Y may exceed the quotient of M/N, and the M out of N criteria may be changed if a preset number of unsuccessful ATP has been actuated by decreasing the quotient M/N or by decreasing N while the quotient M/N is kept constant.

In one or more embodiments, the ICDS may be an implantable cardioverter-defibrillator or a leadless pacer, or may be a system of two or more leadless pacers, or may be a system of at least one leadless pacer and an implantable cardiac pacemaker, or an implantable cardioverter-defibrillator, or an implantable cardiac monitor, or an implantable epicardial pacemaker, or an implantable leadless epicardial pacemaker, or an implantable epicardial cardioverter-defibrillator, or an implantable leadless epicardial cardioverter-defibrillator, or an implantable leadless cardioverter-defibrillator.

In at least one embodiment, the at least one control unit may actuate an ATP prior to an antitachycardiac defibrillation shock if in the VF zone a stable ventricular tachycardia or ventricular arrhythmia is detected and the preset or adaptive M out of N criteria is met.

In at least one embodiment, the actuation may be implemented within an implantable cardioverter-defibrillator system (ICDS), with at least one or more of one or more stimulation units, one or more detection units, one or more control units, wherein the at least one control unit may be connected with the at least one stimulation unit and the at least one control unit may be connected with at the least one detection unit, two or more electrode poles, wherein the two or more electrode poles may be in contact with body tissue, and, one or more high voltage capacitors which may be charged by one or more charging units, and wherein the at least one charging unit may be connected to one or more of the at least one control unit and the at least one stimulation unit, and wherein one or more of the least one control unit and the at least one stimulation unit may initiate the charging of the at least one high voltage capacitor by the at least one charging unit, wherein the at least one detection unit may process physiological signals received from the heart and may detect the presence of an acute ventricular tachycardia or fibrillation, wherein the physiological signals are one or more of accelerations, sounds, and electric signals such as bioelectric potentials, currents and impedances, wherein at least one of the two or more electrode poles may sense electric signals, and wherein the physiological signals or data representing such physiological signals may be transmitted to the control unit by the detection unit utilizing an output signal, wherein the at least control unit may respond to the output signal of the at least detection unit and may actuate the at least one stimulation unit to emit stimulation pulses or a train of stimulation pulses forming an antitachycardic therapy (ATP), or to emit an antitachycardiac defibrillation shock, wherein the at least one control unit may actuate an ATP prior to actuating an antitachycardiac defibrillation shock, wherein the charging of the at least one high voltage capacitor may be initiated either prior to actuating an ATP or during emitting an ATP or after emitting an ATP, wherein the at least control unit may actuate the at least one stimulation unit dependent on preset criteria or an adaptive criteria, wherein the preset or adaptive criteria may be different when actuating an ATP and when actuating an antitachycardiac defibrillation shock, and wherein the criteria when actuating an ATP is a M out of N criteria and the criteria when actuating an antitachycardiac defibrillation shock is a X out of Y criteria, wherein in a default parameter set M=X and N=Y and wherein the X out of Y criteria may be adaptively changed, wherein a parameter of the changed criteria may exhibit X>M and Y>N.

At least one embodiment of the invention allows to adaptively increase the reliability of the tachycardia detection before applying an antitachycardia defibrillation shock without delaying the emitting of the ATP therapy.

By way of one or more embodiments, adaptively changed may include an automatic change, and may also include a change during implantation or aftercare or remotely or combinations thereof.

In one or more embodiments, the two or more electrode poles may be positioned on one or more electrode cables, which are connectable or connected with the ICDS, or the two or more electrode poles may be positioned on one or more implantable devices, wherein at least one of the devices may include an ICDS or ICD or combinations thereof.

According to at least one embodiment, the one or more detection units, the one or more stimulation units and the one or more control units may be, as described, three modules, or the detection unit, the one or more stimulation units and the control unit may be incorporated in a single module or in any number of modules necessary to implement the described functions.

In at least one embodiment of the invention, the quotient of the changed criteria parameter X/Y may exceed the quotient of the changed criteria parameter M/N.

In at least one embodiment, the M out of N criteria may be changed by decreasing the quotient M/N or by decreasing N while the quotient M/N is kept constant, if a preset number of unsuccessful ATP has been actuated.

In one or more embodiments, the quotient of the changed criteria parameter X/Y may exceed the quotient of the changed criteria parameter M/N, and the M out of N criteria may be changed by decreasing the quotient M/N or by decreasing N while the quotient M/N is kept constant, if a preset number of unsuccessful ATP has been actuated.

In at least one embodiment, the ICDS may include an implantable cardioverter-defibrillator, an epicardial pacemaker, an epicardial cardioverter-defibrillator, a leadless epicardial pacemaker, or a leadless epicardial cardioverter-defibrillator. In one or more embodiments, the ICDS may include a leadless pacer or a system of two or more leadless pacers, or a system of at least one leadless pacer and
   an implantable cardiac pacemaker, or
   an implantable cardioverter-defibrillator, or
   an implantable cardiac monitor, or
   an implantable epicardial pacemaker, or
   an implantable leadless epicardial pacemaker, or
   an implantable epicardial cardioverter-defibrillator, or
   an implantable leadless epicardial cardioverter-defibrillator, or
   an implantable leadless cardioverter-defibrillator.

In one or more embodiments, a leadless pacer may also incorporate a leadless implantable cardioverter-defibrillator.

By way of at least one embodiment, an epicardial pacemaker or epicardial cardioverter-defibrillator may be placed in the chest, abdomen or any other suitable part of the body, while at least one electrode pole that stimulates or delivers antitachycardiac defibrillation shock or both may be located on the epicardium. In one or more embodiments, a leadless epicardial pacemaker or leadless epicardial cardioverter-defibrillator may be placed directly on the epicardium.

In at least one embodiment, the at least one control unit may actuate an ATP prior to an antitachycardiac defibrillation shock if in the VF zone a stable ventricular tachycardia or ventricular arrhythmia is detected and the preset or adaptive M out of N criteria is met.

In at least one embodiment, the at least one control unit may detect or verify a VT in the VF-zone prior to charging a high voltage capacitor and after end of charging a high voltage capacitor, but prior to the antitachycardiac defibrillation shock.

In one or more embodiments, the at least one control unit may detect or verify a VT in the VF-zone prior to charging a high voltage capacitor and after end of charging a high voltage capacitor, but prior to the antitachycardiac defibrillation shock delivery, wherein the VT detection with a X out of Y criteria for the detection prior to the charging may be an elongated or prolonged X out of Y criteria, and the VT detection or verification after end of charging a high voltage capacitor, but prior to the antitachycardiac defibrillation shock delivery may be a G out of H criteria, with G≤X and H≤Y.

As the embodiments are for purposes of illustration only, it is apparent to those skilled in the art that numerous modifications and variations and especially combinations of the described examples and embodiments are possible in light of the above and following teaching.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
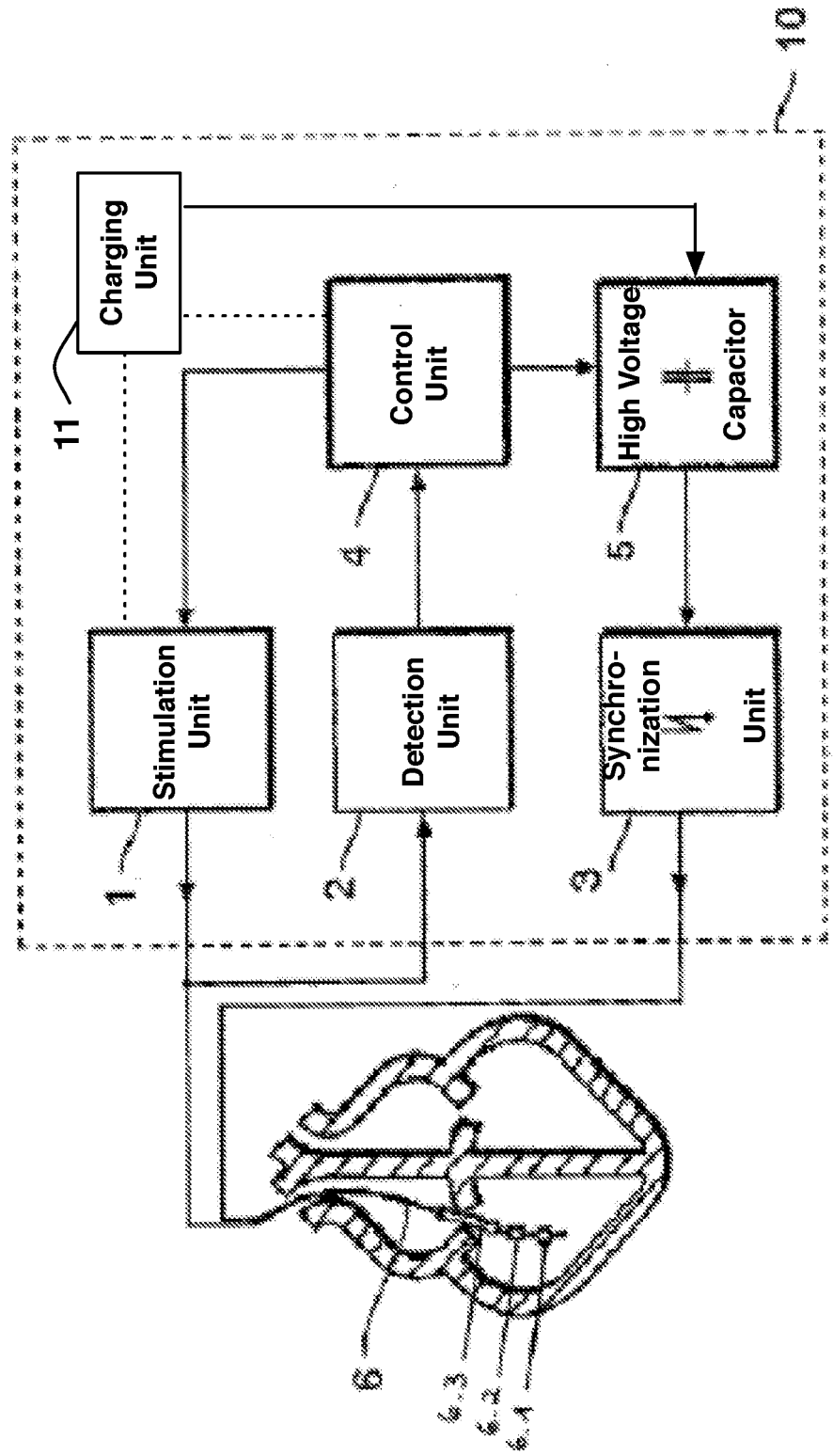
FIG. 1 shows an implantable heart stimulator.

FIG. 1 shows an implantable ICDS or heart stimulator 10, which is connected by an electrode cable 6 to the right ventricle of a heart, according to one or more embodiments of the invention. In at least one embodiment, electrode cable 6 may include three electrode poles, a ventricular tip electrode 6.1 and a ventricular ring electrode 6.2, together with a shock coil 6.3, to emit a defibrillation shock. In one or more embodiments the ventricular tip and ring electrodes 6.1 and 6.2 may include sensing electrodes. In at least one embodiment, ventricular tip electrode 6.1 may also include a stimulation electrode. By way of one or more embodiments, ventricular tip electrode 6.1 and ventricular ring electrode 6.2 may be connected by electrode cable 6 to a detection unit 2 that amplifies the electrical potential received, via electrodes 6.1 and 6.2, using suitable input amplifiers, thereby generating an intracardial electrocardiogram. In at least one embodiment, detection unit 2 may derive a current cardiac frequency from the intracardial electrocardiogram signal and may compare it with predetermined frequency limits. In one or more embodiments, one of the predetermined frequency limits is referred to within the scope of this application as the tachycardia detection limit or fibrillation limit, and corresponds to a cardiac frequency of fibrillation of the heart. In at least one embodiment, detection unit 2 may analyze the stability of the recorded cardiac frequency and may only generate a tachycardia detection signal when the evaluation of the intracardial electrocardiogram indicates that the acute cardiac frequency exceeds the tachycardia detection limit and also fluctuates very little that it conforms to a predetermined stability criterion.

In at least one embodiment, the ICDS 10 may include an implantable cardioverter-defibrillator, an epicardial pacemaker, an epicardial cardioverter-defibrillator, a leadless epicardial pacemaker, or a leadless epicardial cardioverter-defibrillator. In one or more embodiments, the ICDS 10 may include a leadless pacer or a system of two or more leadless pacers, or a system of at least one leadless pacer and an implantable cardiac pacemaker, or an implantable cardioverter-defibrillator, or an implantable cardiac monitor, or an implantable epicardial pacemaker, or an implantable leadless epicardial pacemaker, or an implantable epicardial cardioverter-defibrillator, or an implantable leadless epicardial cardioverter-defibrillator, or an implantable leadless cardioverter-defibrillator. In one or more embodiments, detection unit 2 may be connected to a control unit 4, which responds to a corresponding output signal of detection unit 2.

According to one or more embodiments, control unit 4 may be connected on the output side to a stimulation unit which includes on the one hand a low energy stimulation unit 1 and on the other a defibrillation unit with a high voltage capacitor 5 and a shock synchronization unit 3. In at least one embodiment, the three units, the low energy stimulation unit 1, the high voltage capacitor 5 and the shock synchronization unit 3, may be integrated in a single stimulation unit or may be separated modules or units or may be separated into sub units for different electrode poles or cables or combinations thereof.

In one or more embodiments, low energy stimulation unit 1 may be connected to ventricular tip electrode 6.1 and may emit stimulation pulses of low energy and a maximum voltage of less than 10 volts via ventricular tip electrode 6.1 to a heart. In at least one embodiment, low energy stimulation unit 1, actuated by control unit 4, may emit a fast train of stimulation pulses as antitachycardic therapy with a train frequency of the stimulation pulses which exceeds the acute cardiac frequency detected by detection unit 2. In at least one embodiment, the train of stimulation pulses may then be emitted by low energy stimulation unit 1 when the detection unit 2 generates a tachycardia detection signal after detecting the conditions previously explained and when the detection unit 2 emits the tachycardia detection signal to control unit 4. In one or more embodiments, control unit 4 may initiate charging of high voltage capacitor 5 immediately after the end of a train of stimulation pulses forming the antitachycardic therapy.

In at least one embodiment, detection unit 2 may evaluate the intracardial electrocardiogram recorded immediately after the end of the antitachycardic therapy to determine whether the antitachycardic therapy was successful and whether the tachycardia was terminated as a result. In one or more embodiments, the detector may compare a cardiac frequency derived from the intracardial electrocardiogram after the antitachycardic therapy is given with a frequency limit value, which is herein referred to as the tachycardia detection limit and corresponds to a value which marks the limit between a fast cardiac rhythm not requiring treatment and a low frequency tachycardia with a cardiac cycle length of 600 ms and less. Accordingly, the tachycardia detection limit, in at least one embodiment, may be 100 beats a minute. If the cardiac frequency recorded after the antitachycardic therapy is given is lower than the tachycardia detection limit, in one or more embodiments, the detection unit 2 may generate a tachycardia end signal.

In at least one embodiment, control unit 4 may respond to the tachycardia end signal and may interrupt the charging of high voltage capacitor 5 already begun immediately. According to one or more embodiments, if no tachycardia end is detected until the high voltage capacitor is fully charged, i.e. until the end of charging, and therefore no tachycardia end signal is generated either, charging of high voltage capacitor 5 may be continued until the end of charging, and shock synchronization unit 3 may emit the defibrillation shock, for example in a synchronized manner. In at least one embodiment, the antitachycardiac defibrillation shock may be synchronized to a ventricular heart signal (R-line) or to a ventricular stimulus. In one or more embodiments, the antitachycardiac defibrillation shock may only be emitted unsynchronized if (in the case of an antitachycardiac defibrillation shock without confirmation) no ventricular event occurs within 2 s after the end of charging the high voltage capacitor.

In at least one embodiment, the control unit 4 may emit the antitachycardiac defibrillation shock after the end of charging additionally dependent on the current cardiac frequency then exceeding a tachycardia redetection limit. If in this case the evaluation of the intracardial electrocardiogram recorded after the end of charging of the high voltage capacitor by detection unit 2 indicates that the cardiac frequency lies above the tachycardia redetection limit, according to one or more embodiments, detection unit 2 may generate a tachycardia redetection signal which causes control unit 4 to actuate antitachycardiac defibrillation shock synchronization unit 3, such that detection unit 2 emits an antitachycardiac defibrillation shock that may be synchronized.

As such, in one or more embodiments, ICDS or heart stimulator 10 may terminate a ventricular tachycardia, such as a monomorphous ventricular tachycardia, of high frequency, for example with an antitachycardic therapy, and may initiate an antitachycardiac defibrillation shock as quickly as possible if the antitachycardic therapy is unsuccessful or ineffective, without too much energy for charging a high voltage capacitor being lost in the case of a successful or effective antitachycardic therapy.

In one or more embodiments, the ICDS or heart pacemaker 10 may include various features of implantable heart pacemakers or cardiac monitor or leadless pacer or leadless cardioverters/defibrillators or cardioverters/defibrillators, for example a battery, a charging circuitry included in the at least one charging unit 11, a telemetry unit that transfers data to a service center or to an external device such as a patient device, an atrial stimulation unit, an atrial defibrillation unit, an atrial sensing unit, a left ventricular defibrillation unit, a left ventricular stimulation and/or sensing unit, etc.

Figure 2:
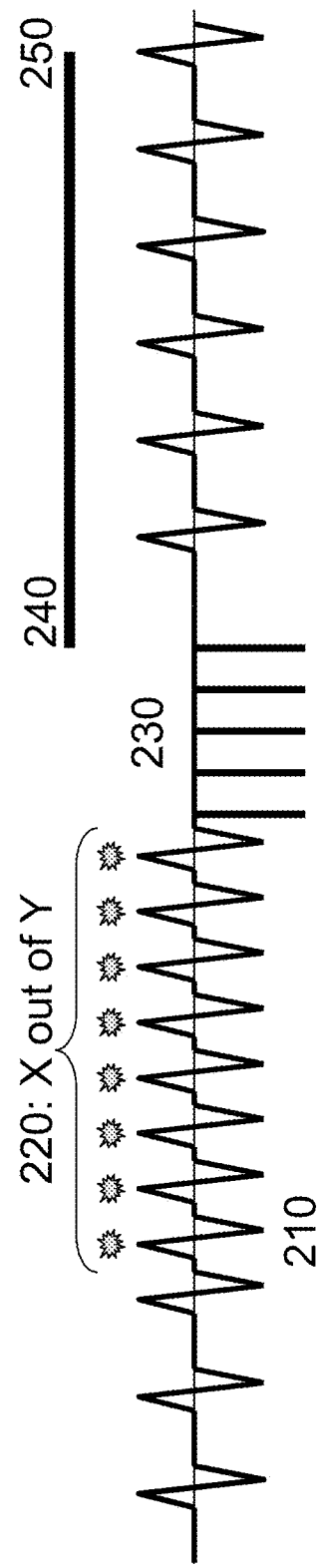
FIG. 2 shows an exemplary intracardiac electrogram (IEGM)

FIG. 2 shows an exemplary intracardiac electrogram (IEGM), according to one or more embodiments, with a X out of Y criteria 220 that detects a stable ventricular tachycardia VT in the VF-Zone 210, an ATP therapy 230, start of charging 240 of a high voltage capacitor with the end of the ATP therapy and end of charging 250 due to an effective ATP, which has terminated the VT in the VF-Zone.

Figure 3:
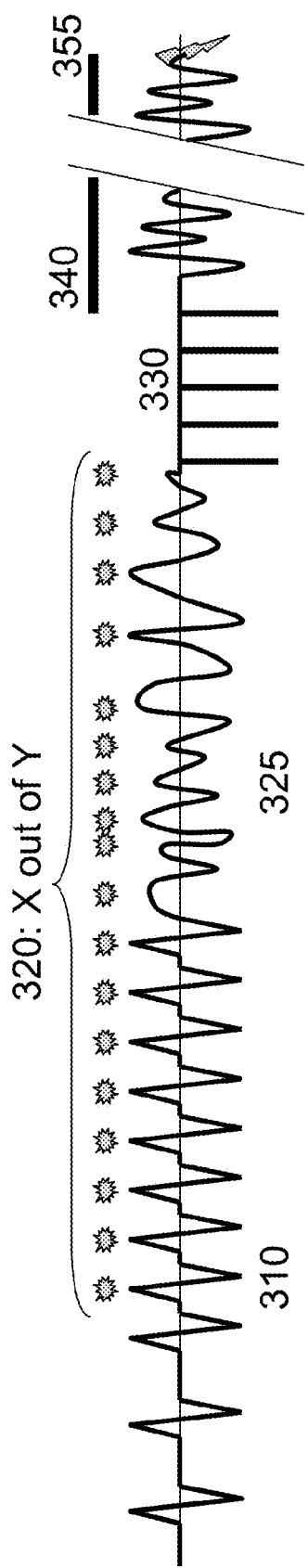
FIG. 3 shows an exemplary IEGM with the drawbacks of a prolonged VT detection.

FIG. 3 visualizes in an exemplary IEGM the drawbacks of a prolonged or elongated VT 310 detection due to a X out of Y criteria 320 with an increased Y or X and Y. As the stable VT degenerates towards an instable VT 325, the ATP therapy 330 may not be able to terminate the VT. Generally, various systems may inhibit the ATP therapy if no stable VT 310 is detected. After the ineffective ATP therapy charging 340 of a high voltage capacitor is started and after the charging of the high voltage capacitor, an antitachycardiac defibrillation shock 355 may be delivered. Even though the prolonged or elongated VT detection may increase the reliability of the VT detection it may also reduce the effectiveness of an ATP therapy.

Figure 4:
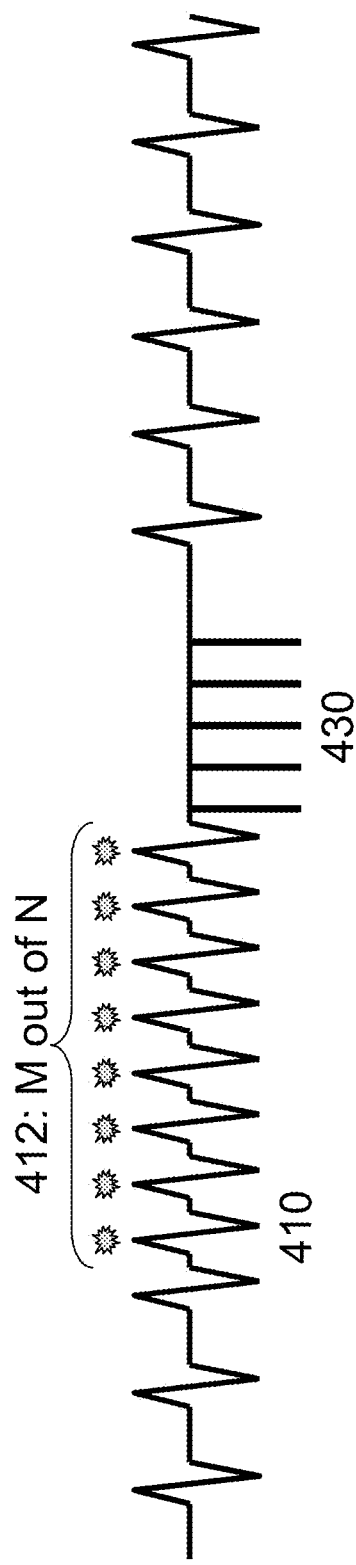
FIG. 4 shows an exemplary IEGM with a M out of N criteria.

FIG. 4 shows in an exemplary IEGM an embodiment with a M out of N criteria 412, a stable VT in the VF zone and an effective delivery of an ATP therapy 430, according to one or more embodiments of the invention. In at least one embodiment, after the ATP therapy 430, a regular heart rhythm may be visible on right side from the ATP stimuli 430 in FIG. 4. In one or more embodiments, due to the regular heart rhythm after the ATP therapy, an antitachycardiac defibrillation shock may not be necessary. The VF detection after the ATP therapy is not shown.

Figure 5:
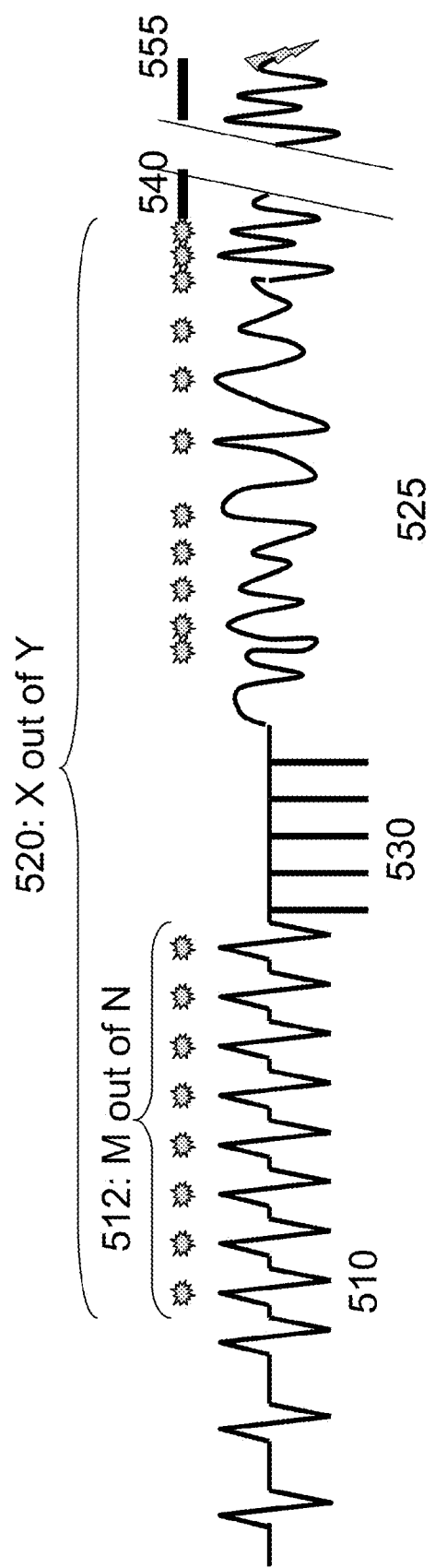
FIG. 5 shows an exemplary IEGM with different criteria for VT detection.

FIG. 5 visualizes in an exemplary IEGM, according to one or more embodiments, where stable VT 510 in the VF zone may not be terminated by an ATP therapy 530 and the stable VT 510 degenerates to an unstable VT 525. Even though the VT detection is realized with a short M out of N criteria, in at least one embodiment, the VT is still a stable VT 510, the ATP therapy may be not able to terminate the VT and the VT degenerates to an instable VT 525.

In one or more embodiments, a prolonged VT detection for antitachycardiac defibrillation shock delivery with a X out of Y criteria 520 with at least a larger Y than N, or a X out of Y criteria with at a larger X than M and Y than N, was started with the VT X out of Y detection for ATP therapy 530 and continued after delivery the ATP therapy 530. At the end of the VT detection with the X out of Y criteria 520, according to one or more embodiments, the charging of at least one high voltage capacitor is started at 540, and when charging is finished an antitachycardiac defibrillation shock 555 is delivered. In at least one embodiment, the prolonged VT detection utilizing a M out of N criteria 520 with at least a larger Y than N or a X out of Y criteria with at a larger X than M and Y than N may make the VT detection more reliable, while the shorter VT detection with the λ out of Y criteria enables a fast ATP therapy delivery, increasing the possibility of an effectively delivered ATP therapy.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS

1: low energy stimulation unit or stimulation unit
2: detection unit
3: synchronization unit
4: control unit
5: high voltage capacitor
6: electrode cable
6.1: tip electrode pole
6.2: ring electrode pole
6.3: shock coil for delivering a high voltage antitachycardiac defibrillation shock
10: ICDS or heart stimulator or ICD
210: start of a stable ventricular tachycardia in the ventricular fibrillation- (VF-)zone
220: short X out of Y criteria, here shown a fulfilled 8 out of 12 criteria
230: ATP therapy also known as ATP one shot
240: start of charging of a high voltage capacitor with the end of the ATP therapy
250: end of charging of a high voltage capacitor due to an effective ATP
310: start of a stable ventricular tachycardia in the ventricular fibrillation- (VF-)zone
320: elongated or prolonged VT detection due to a X out of Y criteria with increased Y and/or X
325: stable VT degenerates towards an instable VT
330: ineffective ATP therapy, which may be even suppressed by some systems
340: start of charging of a high voltage capacitor with the end of the ATP therapy
355: end of charging of a high voltage capacitor and delivery of an antitachycardiac defibrillation shock due to an ineffective ATP
410: start of a stable ventricular tachycardia in the ventricular fibrillation- (VF-)zone
412: short M out of N criteria for VT detection and for triggering the ATP therapy
430: delivery of ATP therapy
510: start of a stable ventricular tachycardia in the ventricular fibrillation- (VF-)zone
512: short M out of N criteria for VT detection and for triggering the ATP therapy
520: elongated or prolonged VT detection due to a X out of Y criteria with increased Y and/or X for triggering an antitachycardiac defibrillation shock delivery
530: delivery of ATP therapy, which is ineffective
540: start of charging of a high voltage capacitor, triggered by the elongated or prolonged VT detection with the elongated or prolonged λ out of Y criteria
555: end of charging of a high voltage capacitor and delivery of an antitachycardiac defibrillation shock due to an ineffective ATP therapy

What is claimed is:

1. An implantable cardioverter-defibrillator system (ICDS) comprising:
   at least one stimulation unit;
   at least one detection unit;
   at least one control unit;
      wherein the at least one control unit is connected with the at least one stimulation unit, and
      wherein the at least one control unit is connected with the at least one detection unit;
   at least two electrode poles connected to the at least one detection unit, wherein the at least two electrode poles are in contact with body tissue;
   at least one high voltage capacitor that is configured to be charged by at least one charging unit, wherein the at least one high voltage capacitor is connected to the at least one control unit and wherein the at least one charging unit is connected to the at least one high voltage capacitor;
      wherein the at least one charging unit is connected to one or more of the at least one control unit and the at least one stimulation unit, and wherein one or more of the least one control unit and the at least one stimulation unit is is configured to initiate the charging of the at least one high voltage capacitor by the at least one charging unit;

wherein the at least one detection unit is configured to process physiological signals received from the heart and to detect the presence of an acute ventricular tachycardia or fibrillation, wherein said physiological signals comprise one or more of accelerations, sounds, and electric signals comprising one or more of bioelectric potentials, currents and impedances;

wherein at least one of the at least two electrode poles is configured to sense electric signals;

wherein the physiological signals or data representing said physiological signals are transmitted to the control unit by the detection unit utilizing an output signal;

wherein the at least one control unit is configured to respond to the output signal of the at least one detection unit and to actuate the at least one stimulation unit to emit stimulation pulses or a train of stimulation pulses forming an antitachycardic therapy (ATP), or to emit an antitachycardiac defibrillation shock;

wherein the at least one control unit is further configured to actuate an ATP prior to actuating an antitachycardiac defibrillation shock;

wherein the charging of the at least one high voltage capacitor is initiated either prior to actuating an ATP or during emitting an ATP or after emitting an ATP;

wherein the at least one control unit is configured to actuate the at least one stimulation unit dependent on preset criteria or an adaptive criteria;

wherein the preset or adaptive criteria is different when actuating an ATP and when actuating an antitachycardiac defibrillation shock, and, wherein the preset or adaptive criteria when actuating an ATP is from the physiological signals or data representing said physiological signals a detection of a first number of events M out of a first total number of events N criteria with an M/N quotient, and the preset or adaptive criteria when actuating an antitachycardiac defibrillation shock is from the physiological signals or data representing said physiological signals a detection of a second number of events X out of a second total number of events Y criteria with an X/Y quotient, wherein at least X>M and Y>N.

2. The implantable cardioverter-defibrillator system of claim 1, wherein the quotient of X/Y exceeds the quotient of M/N.

3. The implantable cardioverter-defibrillator system of claim 2, wherein the M out of N criteria is changed if a preset number of unsuccessful ATP has been actuated by decreasing the quotient M/N or by decreasing N while the quotient M/N is kept constant.

4. The implantable cardioverter-defibrillator system of claim 1, wherein the M out of N criteria is changed if a preset number of unsuccessful ATP has been actuated by decreasing the quotient M/N or by decreasing N while the quotient M/N is kept constant.

5. The implantable cardioverter-defibrillator system of claim 1, comprising an implantable cardioverter-defibrillator.

6. The implantable cardioverter-defibrillator system of claim 1, comprising a leadless pacer.

7. The implantable cardioverter-defibrillator system of claim 1, comprising a system of two or more leadless pacers, or
a system of at least one leadless pacer and
an implantable cardiac pacemaker, or
an implantable cardioverter-defibrillator, or
a leadless implantable cardioverter-defibrillator, or
an implantable cardiac monitor, or
an implantable epicardial pacemaker, or
an implantable leadless epicardial pacemaker,
or an implantable epicardial cardioverter-defibrillator, or
an implantable leadless epicardial cardioverter-defibrillator.

8. The implantable cardioverter-defibrillator system of claim 1, wherein the at least one control unit is configured to actuate the ATP prior to an antitachycardiac defibrillation shock if in the VF zone a stable ventricular tachycardia or ventricular arrhythmia is detected and the preset or adaptive M out of N criteria is met.

9. An implantable cardioverter-defibrillator system (ICDS) comprising:
at least one stimulation unit;
at least one detection unit;
at least one control unit;
wherein the at least one control unit is connected with the at least one stimulation unit, and
wherein the at least one control unit is connected with the at least one detection unit;
at least two electrode poles connected to the at least one detection unit, wherein the at least two electrode poles are in contact with body tissue;
at least one high voltage capacitor that is configured to be charged by at least one charging unit, wherein the at least one high voltage capacitor is connected to the at least one control unit and wherein the at least one charging unit is connected to the at least one high voltage capacitor;
wherein the at least one charging unit is connected to one or more of the at least one control unit and the at least one stimulation unit, and
wherein one or more of the least one control unit and the at least one stimulation unit is configured to initiate the charging of the at least one high voltage capacitor by the at least one charging unit;
wherein the at least one detection unit is configured to process physiological signals received from the heart and to detect the presence of an acute ventricular tachycardia or fibrillation, wherein said physiological signals are one or more of accelerations, sounds, and electric signals comprising one or more of bioelectric potentials, currents and impedances;
wherein at least one of the at least two electrodes poles is configured to sense electric signals;
wherein the physiological signals or data representing said physiological signals are transmitted to the control unit by the detection unit utilizing an output signal;
wherein the at least one control unit is configured to respond to the output signal of the at least one detection unit and to actuate the at least one stimulation unit to emit stimulation pulses or a train of stimulation pulses forming an antitachycardic therapy (ATP), or to emit an antitachycardiac defibrillation shock;
wherein the at least one control unit is further configured to actuate an ATP prior to actuating an antitachycardiac defibrillation shock;
wherein the charging of the at least one high voltage capacitor is initiated either prior to actuating an ATP or during emitting an ATP or after emitting an ATP; and, wherein the at least one control unit is configured to actuate the at least one stimulation unit dependent on preset criteria or an adaptive criteria;

wherein the preset or adaptive criteria is different when actuating an ATP and when actuating an antitachycardiac defibrillation shock, and, wherein the preset or adaptive criteria when actuating an ATP is from the physiological signals or data representing said physiological signals a detection of a first number of events M out of a first total number of events N criteria with an M/N quotient, and the preset or adaptive criteria when actuating an antitachycardiac defibrillation shock is from the physiological signals or data representing said physiological signals a detection of a second number of events X out of a second total number of events Y criteria with an X/Y quotient, wherein in a default parameter set M=X and N=Y, and wherein the X out of Y criteria is adaptively changed with a parameter of the criteria adaptively exhibiting X>M and Y>N.

10. The implantable cardioverter-defibrillator system of claim 9, wherein a quotient of the changed criteria parameter X/Y exceeds a quotient of the changed criteria parameter M/N.

11. The implantable cardioverter-defibrillator system of claim 10, wherein the M out of N criteria is changed by decreasing the quotient M/N or by decreasing N while the quotient M/N is kept constant, if a preset number of unsuccessful ATP has been actuated.

12. The implantable cardioverter-defibrillator system of claim 9, wherein the M out of N criteria is changed by decreasing the quotient M/N or by decreasing N while the quotient M/N is kept constant, if a preset number of unsuccessful ATP has been actuated.

13. The implantable cardioverter-defibrillator system of claim 9, comprising an implantable cardioverter-defibrillator.

14. The implantable cardioverter-defibrillator system of claim 9, comprising a leadless pacer.

15. The implantable cardioverter-defibrillator system of claim 9, comprising
a system of two or more leadless pacers, or
a system of at least one leadless pacer and
an implantable cardiac pacemaker, or
an implantable cardioverter-defibrillator, or
a leadless implantable cardioverter-defibrillator, or
an implantable cardiac monitor, or
an implantable epicardial pacemaker, or
an implantable leadless epicardial pacemaker, or
an implantable epicardial cardioverter-defibrillator, or
an implantable leadless epicardial cardioverter-defibrillator.

16. The implantable cardioverter-defibrillator system of claim 15, wherein the at least one control unit is configured to actuate the ATP prior to an antitachycardiac defibrillation shock if in the VF zone a stable ventricular tachycardia or ventricular arrhythmia is detected and the preset or adaptive M out of N criteria is met.

* * * * *